United States Patent [19]

Hausberg et al.

[11] Patent Number: 4,698,351

[45] Date of Patent: Oct. 6, 1987

[54] TETRAHYDROCARBAZOLE DERIVATIVES AND PHARMACEUTICAL COMPOSITIONS

[75] Inventors: Hans-Heinrich Hausberg, Ober-Ramstadt; Henning Böttch, Darmstadt; Rudolf Gottschlich, Reinheim; Christoph Seyfried, Seeheim-Jugenheim; Klaus-Otto Minck, Ober-Ramstadt, all of Fed. Rep. of Germany

[73] Assignee: Merck Patent Gesellschaft mit beschraenkter Haftung, Darmstadt, Fed. Rep. of Germany

[21] Appl. No.: 899,453

[22] Filed: Aug. 22, 1986

Related U.S. Application Data

[62] Division of Ser. No. 818,859, Jan. 15, 1986, Pat. No. 4,618,614, which is a division of Ser. No. 747,594, Jul. 24, 1985, abandoned, which is a division of Ser. No. 568,310, Jan. 4, 1984, Pat. No. 4,547,756.

Foreign Application Priority Data

[30]

Jan. 4, 1983 [DE] Fed. Rep. of Germany ....... 3300094
Oct. 8, 1983 [DE] Fed. Rep. of Germany ....... 3336643

[51] Int. Cl.$^4$ .................... A61K 31/44; C07D 401/06; C07D 491/056
[52] U.S. Cl. .................................... 514/338; 514/339; 546/270; 546/272
[58] Field of Search ................. 546/270, 272; 514/338, 514/339

[56] References Cited

U.S. PATENT DOCUMENTS 3,634,420 1/1972 Littell et al. .................... 548/439
3,740,404 6/1973 Littell et al. .................... 546/200

Primary Examiner—Robert W. Ramsuer
Attorney, Agent, or Firm—Millen & White

[57] ABSTRACT

Tetrahydrocarbazole derivatives of the general formula I

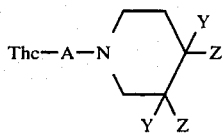

in which Thc is a 1,2,3,4-tetrahydro-3-carbazolyl radical which can be substituted once or twice by alkyl, O-alkyl, S-alkyl, SO-alkyl, $SO_2$-alkyl, OH, F, Cl, Br, $CF_3$ and/or CN or by a methylenedioxy group, the two radicals Y are each H or together are a C-C bond, one radical Z is Ar and the other radical Z is H, A is —$CH_2$— or —$CH_2CH_2$— and Ar is a phenyl group which is unsubstituted or substituted once or twice by alkyl, O-alkyl, S-alkyl, SO-alkyl, $SO_2$-alkyl, OH, F, Cl, Br, $CF_3$ and/or CN or by a methylenedioxy group, or is a 2- or 3-thienyl radical, and in which the alkyl groups each have 1–4 C atoms, and their physiologically acceptable acid addition salts have effects on the central nervous system.

15 Claims, No Drawings

TETRAHYDROCARBAZOLE DERIVATIVES AND PHARMACEUTICAL COMPOSITIONS

This is a division of application Ser. No. 818,859 filed Jan. 15, 1986, which is a division of Ser. No. 747,594 filed Jul. 24, 1985, now abandoned which is a division of Ser. No. 568,310 filed Jan. 4, 1984, now U.S. Pat. No. 4,547,756.

The invention relates to new tetrahydrocarbazole derivatives.

SUMMARY OF THE INVENTION

It is an object of this invention to provide new compounds which can be used for producing valuable medicaments.

Upon further study of the specification and appended claims, further objects and advantages of this invention will become apparent to those skilled in the art.

These objects have been achieved by providing compounds of formula I

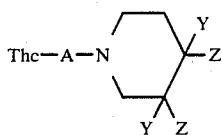

in which Thc is a 1,2,3,4-tetrahydro-3-carbazolyl radical which can be substituted once or twice by alkyl, O-alkyl, S-alkyl, SO-alkyl, $SO_2$-alkyl, OH, F, Cl, Br, $CF_3$ and/or CN or by a methylenedioxy group, the two radicals Y are each H or together are a C-C bond, one radical Z is Ar and the other radical Z is H, A is $-CH_2-$ or $-CH_2CH_2-$ and Ar is a phenyl group which is unsubstituted or is substituted once or twice by alkyl, O-alkyl, S-alkyl, SO-alkyl, $SO_2$-alkyl, OH, F, Cl, Br, $CF_3$ and/or CN or by a methylenedioxy group, or is a 2- or 3-thienyl radical, and in which the alkyl groups each have 1-4 C atoms, and their physiologically acceptable acid addition salts.

It has been found that the compounds of the formula I and their physiologically acceptable acid addition salts have valuable pharmacological properties. Thus, in particular, they have effects on the central nervous system, especially dopamine-stimulating (antiparkinsonism) effects. Specifically, the compounds of the formula I induce contralateral turning behaviour in rats with hemiparkinsonism (which may be demonstrated by the method of Ungerstedt et al., Brain Res. 24, (1970), 485–493) and they inhibit the binding of tritiated dopamine agonists and antagonists to striatal receptors (which may be demonstrated by the method of Schwarcz et al., J. Neurochemistry, 34, (1980), 772–778 and Creese et al., European J. Pharmacol., 46, (1977), 377–381). In addition, the compounds inhibit the linguomandibular reflex in the anaesthetised rat (which may be demonstrated by methods derived from Barnett et al., European J. Pharmacol. 21, (1973), 178–182, and from Ilhan et al., European J. Pharmacol. 33, (1975) 61–64). Moreover, analgesic and hypotensive effects occur; thus after intragastric administration of the compounds, the directly measured arterial blood pressure of catheterized, conscious spontaneously hypertensive rats (strain SHR/NIH-MO/CHB-EMD; for method, see Weeks and Jones, Proc. Soc. Exptl. Biol. Med. 104, (1960), 646–648) is decreased.

Thus, compounds of the formula I and their physiologically acceptable acid addition salts can be used as active compounds in medicaments and also as intermediate products for the preparation of other active compounds in medicaments.

The invention relates to the tetrahydrocarbazole derivatives of the formula I and their physiologically acceptable acid addition salts.

DETAILED DISCUSSION

In the radicals Thc and Ar, alkyl is preferably methyl, but is also ethyl, n-propyl, isopropyl, n-butyl, isobutyl, sec.-butyl or tert.-butyl. O-Alkyl is preferably methoxy, but is also ethoxy, n-propoxy, isopropoxy, n-butoxy, isobutoxy, sec.-butoxy or tert.-butoxy, S-alkyl is preferably methylthio, but is also ethylthio, n-propylthio, isopropylthio, n-butylthio, isobutylthio, sec.-butylthio or tert.-butylthio. SO-Alkyl is preferably methylsulfinyl, but is also ethylsulfinyl, n-propylsulfinyl, isopropylsulfinyl, n-butylsulfinyl, isobutylsulfinyl, sec.-butylsulfinyl or tert.-butylsulfinyl. $SO_2$-Alkyl is preferably methylsulfonyl, but is also ethylsulfonyl, n-propylsulfonyl, isopropylsulfonyl, n-butylsulfonyl, isobutylsulfonyl, sec.-butylsulfonyl or tert.-butylsulfonyl.

The radical Thc is, in particular, an unsubstituted 1,2,3,4-tetrahydro-3-carbazolyl radical. However, if Thc is a substituted 1,2,3,4-tetrahydro-3-carbazolyl radical, then it is preferably substituted once, in particular in the 6- or 7-position. Substitution is also possible at the 1-, 2-, 3-, 4-, 5-, 8- or 9-position. Preferred disubstituted 1,2,3,4-tetrahydro-3-carbazolyl radicals are substituted in the 6,7-positions; disubstitution is also possible in the 1,1-, 1,2-, 1,3-, 1,4-, 1,5-, 1,6-, 1,7-, 1,8-, 1,9-, 2,2-, 2,3-, 2,4-, 2,5-, 2,6-, 2,7-, 2,8-, 2,9-, 3,4-, 3,5-, 3,6-, 3,7-, 3,8-, 3,9-, 4,4-, 4,5-, 4,6-, 4,7-, 4,8-, 4,9-, 5,6-, 5,7-, 5,8-, 5,9-, 6,8-, 6,9-, 7,8-, 7,9- or 8,9-positions. In all these cases, the substituents can be identical or different.

Specifically, the preferred substituents in the benzene ring in the radical Thc are methyl, ethyl, methoxy, ethoxy, methylthio, ethylthio, OH, F, Cl, Br, $CF_3$ and CN. Accordingly, some preferred meanings of the radical Thc are 1,2,3,4-tetrahydro-3-carbazolyl, -also 1-, 2-, 3-, 4-, 5-, 6-, 7-, 8- or 9-methyl-1,2,3,4-tetrahydro-3-carbazolyl, 1-, 2-, 3-, 4-, 5-, 6-, 7-, 8- or 9-ethyl-1,2,3,4-tetrahydro-3-carbazolyl, 5-, 6-, 7- or 8-methoxy-1,2,3,4-tetrahydro-3-carbazolyl, 5-, 6-, 7- or 8-ethoxy-1,2,3,4-tetrahydro-3-carbazolyl, 5-, 6-, 7- or 8-methylthio-1,2,3,4-tetrahydro-3-carbazolyl, 5-, 6-, 7-or 8-ethylthio-1,2,3,4-tetrahydro-3-carbazolyl, 5-, 6-, 7- or 8-methylsulfinyl-1,2,3,4-tetrahydro-3-carbazolyl, 5-, 6-, 7- or 8-methylsulfonyl-1,2,3,4-tetrahydro-3-carbazolyl, 5-, 6-, 7- or 8-hydroxy-1,2,3,4-tetrahydro-3-carbazolyl, 5-, 6-, 7- or 8-fluoro-1,2,3,4-tetrahydro-3-carbazolyl, 5-, 6-, 7- or 8-chloro-1,2,3,4-tetrahydro-3-carbazolyl, 5-, 6-, 7- or 8-bromo-1,2,3,4-tetrahydro-3carbazolyl, 5-, 6-, 7- or 8-trifluoromethyl-1,2,3,4-tetrahydro-3-carbazolyl, 5-, 6-, 7- or 8-cyano-1,2,3,4-tetrahydro-3-carbazolyl, 1,2-, 1,4-, 1,5-, 1,6-, 1,7-, 1,8-, 1,9-, 2,4-, 2,5-, 2,6-, 2,7-, 2,8-, 2,9-, 4,5-, 4,6-, 4,7-, 4,8-, 4,9-, 5,6-, 5,7-, 5,8-, 5,9-, 6,7-, 6,8-, 6,9-, 7,8-, 7,9- or 8,9-dimethyl-1,2,3,4-tetrahydro-3-carbazolyl, 5-, 6-, 7- or 8-methoxy-9-methyl-1,2,3,4-tetrahydro-3-carbazolyl, 5-, 6-, 7- or 8-methylthio-9-methyl-1,2,3,4-tetrahydro-3-carbazolyl, 5-, 6-, 7- or 8-fluoro-9-methyl-1,2,3,4-tetrahydro-3-carbazolyl, 5-, 6-, 7- or 8-chloro-9-methyl-1,2,3,4-tetrahydro-3-carbazolyl, 5-, 6-, 7- or 8-bromo-9-methyl-1,2,3,4-tetrahydro-3-carbazolyl, 5-, 6-, 7- or 8-trifluoromethyl-9-methyl-1,2,3,4-tetrahydro-3-carbazolyl, 5-, 6-, 7- or 8-cyano-9-methyl- 1,2,3,4-tetrahydro-3-carbazolyl, 1- or 2-methyl-5-, -6-, -7- or -8-methoxy-1,2,3,4-tetrahydro-3-carbazolyl, 1- or 2-methyl-5-, -6-, -7- or -8-methylthio-1,2,3,4-tetrahydro-3-carbazolyl, 1- or 2-methyl-5-, -6-, -7- or -8-fluoro-1,2,3,4-tetrahydro-3-carbazolyl, 1- or 2-methyl-5-, -6-, -7- or -8-chloro-1,2,3,4-tetrahydro-3carbazolyl, 1- or 2-methyl-5-, -6-, -7- or -8-bromo-1,2,3,4-tetrahydro-3-carbazolyl, 1- or 2-methyl-5-, -6-, -7- or -8-trifluoromethyl-1,2,3,4-tetrahydro-3-carbazolyl, 1- or 2-methyl-5-, -6-, -7- or -8-cyano-1,2,3,4-tetrahydro-3-carbazolyl, 6-methyl-7-fluoro-1,2,3,4-tetrahydro-carbazolyl, 6-fluoro-7- or -9-methyl-1,2,3,4-tetrahydro-3-carbazolyl, 6-methyl-7-chloro-1,2,3,4-tetrahydro-3-carbazolyl, 6-chloro-7-methyl-1,2,3,4-tetrahydro-3carbazolyl, 5-chloro-6-.or -7-methyl-1,2,3,4-tetrahydro-3-carbazolyl, 5,6-, 5,7-, 5,8-, 6,7-, 6,8- or 7,8-dimethoxy-1,2,3,4-tetrahydro-3-carbazolyl, 5,6-, 5,7-, 5,8-, 6,7-, 6,8- or 7,8-dichloro-1,2,3,4-tetrahydro-3-carbazolyl, 5-trifluoromethyl-6-, -7- or -8-chloro-1,2,3,4-tetrahydro-3-carbazolyl, 5,6-, 6,7- or 7,8-methylenedioxy-1,2,3,4-tetrahydro-3-carbazolyl.

The radical A is preferably —CH$_2$—.

The radical Ar is preferably unsubstituted phenyl. When Ar is a substituted phenyl group, then it is preferably substituted once. However, it can also be substituted twice, it being possible for the substituents to be identical or different. Preferred substituents on the phenyl group are methyl, F, Cl, Br and trifluoromethyl. Specifically, Ar is preferably phenyl, o-, m-or p-fluorophenyl, o-, m- or p-chlorophenyl, o-, m- or p-bromophenyl, o-, m- or p-tolyl, o-, m- or p-methoxyphenyl, o-, m- or p-trifluoromethylphenyl, also, for example, o-, m- or p-ethylphenyl, o-, m- or p-n-propylphenyl, o-, m- or p-isopropylphenyl, o-, m- or p-n-butylphenyl, o-, m- or p-isobutylphenyl, also dihalogenophenyl, such as 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4-or 3,5-dibromophenyl, 2-fluoro-4-chlorophenyl, 2-bromo-4chlorophenyl; dimethylphenyl, such as 2,3-, 2,4-, 2,5-, 2,6-, 3,4- or 3,5-dimethylphenyl; methylchlorophenyl, such as 2-methyl-4-chlorophenyl; dimethoxyphenyl, such as 2,3-, 2,4-, 2,5-, 2,6-, 3,4- or 3,5-dimethoxyphenyl; 2,3- or 3,4-methylenedioxyphenyl.

Accordingly, the invention particularly relates to those compounds of the formula I in which at least one of the radicals mentioned has one of the meanings indicated above, especially one of the preferred meanings indicated above. Some preferred groups of compounds can be expressed by the following formulae Ia to Ig which correspond to the formula I and wherein the radicals which are not specified have the meaning indicated for formula I, but wherein in Ia, Thc is 1,2,3,4-tetrahydro-3-carbazolyl, methyl-1,2,3,4-tetrahydro-3-carbazolyl, methoxy-1,2,3,4-tetrahydro-3-carbazolyl, dimethoxy-1,2,3,4-tetrahydro-3carbazolyl, hydroxy-1,2,3,4-tetrahydro-3-carbazolyl, dihydroxy-1,2,3,4-tetrahydro-3-carbazolyl, fluoro-1,2,3,4-tetrahydro-3-carbazolyl, chloro-1,2,3,4-tetrahydro-3carbazolyl, dichloro-1,2,3,4-tetrahydro-3-carbazolyl, bromo-1,2,3,4-tetrahydro-3-carbazolyl, cyano-1,2,3,4-tetrahydro-3-carbazolyl or methylenedioxy-1,2,3,4-tetrahydro-3-carbazolyl, the substituents preferably being in the 6- and/or 7-position; in Ib, Thc is 1,2,3,4-tetrahydro-3-carbazolyl, 6- or 7-methyl-1,2,3,4-tetrahydro-3-carbazolyl, 6,7-dimethyl-1,2,3,4-tetrahydro-3-carbazolyl, 6- or 7-methoxy-1,2,3,4-tetrahydro-3-carbazolyl, 6,7-dimethoxy-1,2,3,4-tetrahydro-3-carbazolyl, 6- or 7-chloro-1,2,3,4-tetrahydro-3-carbazolyl, 6- or 7-hydroxy-1,2,3,4-tetrahydro-3-carbazolyl, 6,7-dihydroxy-1,2,3,4-tetrahydro-3-carbazolyl or 6,7-methylenedioxy-1,2,3,4-tetrahydro-3-carbazolyl; in Ic, A is —CH$_2$—; in Id, Ar is phenyl, tolyl, methoxyphenyl, fluorophenyl, chlorophenyl, trifluoromethylphenyl or chlorotrifluoromethylphenyl; in Ie, Ar is phenyl, in If, Thc is 1,2,3,4-tetrahydro-3-carbazolyl, 6- or 7-methoxy-1,2,3,4-tetrahydro-3-carbazolyl, 6- or 7-hydroxy-1,2,3,4-tetrahydro-3-carbazolyl, 6,7-dimethoxy-1,2,3,4-tetrahydro-3-carbazolyl, 6- or 7-chloro-1,2,3,4-tetrahydro-3-carbazolyl or 6,7-dihydroxy-1,2,3,4-tetrahydro-3-carbazolyl and Ar is phenyl; in Ig, Thc is 1,2,3,4-tetrahydro-3-carbazolyl, 6- or 7-hydroxy-1,2,3,4-tetrahydro-3-carbazolyl, A is —CH$_2$— and Ar is phenyl.

The compounds of the formula I have an asymmetric carbon atom in the 3-position of the tetrahydrocarbazole ring. They can also have other asymmetric carbon atoms. Thus, they can exist as racemates and, if several asymmetric carbon atoms are present, they can also exist as mixtures of several racemates and in various optically active forms.

The invention also relates to a process for the preparation of the compounds of the formula I and of their physiologically acceptable acid addition salts, which is characterised in that a compound of the general formula II

$$\text{Thc}-A-X^1 \qquad \text{II}$$

in which $X^1$ is X or NH$_2$ and X is Cl, Br, I, OH or a reactive derivative of an OH group, and Thc and A have the meanings indicated, is reacted with a compound of the general formula III

in which $X^2$ and $X^3$ can be identical or different and, when $X^1$ is NH$_2$, are both X, but otherwise are together NH, and Y and Z have the meaning indicated, or in that a compound which corresponds to the formula I, apart from containing one or more reducible group(s) and/or one or more additional C-C and/or C-N bond(s) in place of one or more hydrogen atoms, is treated with a reducing agent, or in that a compound corresponding to the formula I, apart from containing one or more group(s) which can be eliminated by solvolysis in place of one or more hydrogen atoms, is treated with a solvolysing agent, or in that, to prepare compounds of the formula I in which the two radicals Y are together a C-C bond, a compound of the formula IV

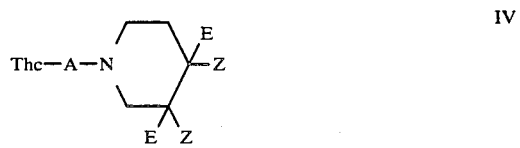

in which one radical E is X, CN or NH$_2$, and the other radical E is H, and Thc, A, X and Z have the meanings indicated, is treated with an agent which eliminates HE, and/or in that, where appropriate in a compound of the formula I, a thioether group is oxidized to a SO group or SO₂ group, or a SO group is oxidized to a SO₂ group, and/or an alkoxy group is cleaved with formation of an OH group, and/or a C-C double bond is hydrogenated, and/or in that a resulting base of the formula I is converted into one of its physiologically acceptable acid addition salts by treatment with an acid.

The preparation of the compounds of the formula I is otherwise carried out by methods known per se, as are described in the literature (for example in the standard works, such as Houben-Weyl, Methoden der Organischen Chemie (Methods of Organic Chemistry), Georg-Thieme-Verlag, Stuttgart: Organic Reactions, John Wiley & Sons, Inc., New York), namely under reaction conditions as are known and suitable for the reactions mentioned. Use can also be made in these preparations of variants known per se which are not mentioned in more detail here.

The starting materials can, if desired, also be formed in situ in such a manner that they are not isolated from the reaction mixture but are immediately reacted further to give the compounds of the formula I.

In the tetrahydrocarbazole derivatives of the formula II, $X^1$ is preferably X; accordingly, in the compounds of the formula III, $X^2$ and $X^3$ together are preferably NH. The radical X is preferably Cl or Br; however, it can also be I, OH or a reactive derivative of an OH group, in particular alkylsulfonyloxy having 1-6 (for example methanesulfonyloxy), or arylsulfonyloxy having 6-10 C atoms (for example benzenesulfonyloxy, p-toluenesulfonyloxy, 1- or 2-naphthalenesulfonyloxy).

Accordingly, the tetrahydrocarbazole derivatives of the formula I can be obtained, in particular, by reaction of the compounds of the formula Thc-A-Cl or Thc-A-Br with piperidine derivatives of the formula III, in which $X^2$ and $X^3$ together are a NH group (denoted by IIIa in the following text).

Some of the compounds of the formulae II and, in particular, III are known; the unknown compounds of the formulae II and III can be easily prepared in analogy to the known compounds from known or readily prepared starting materials.

Thus, the compounds of the formula II (A=—CH₂—) can be obtained, for example, by reducing the carboxylic acids of the formula Thc-COOH, which are generally known and can be prepared from the corresponding phenylhydrazines and the corresponding cyclohexanone-4-carboxylic esters by means of the Fischer indole synthesis, to give the corresponding carbinols of the formula Thc—CH₂OH, and converting the latter, for example with SOCl₂, into the corresponding chlorides of the formula Thc-CH₂Cl or, for example with PBr₃, into the corresponding bromides of the formula Thc—CH₂Br. Reaction of the last-mentioned chlorides or bromides with KCN leads to the acetonitriles of the formula Thc—CH₂CN, which can be hydrolyzed to give the acetic acids of the formula Thc—CH₂COOH. Reduction and further analogous reactions provide compounds of the formulae Thc—CH₂CH₂OH, Thc—CH₂CH₂Cl and Thc—CH₂CH₂Br.

The iodine compounds of the formula Thc-A-I, for example 3-iodomethyl-1,2,3,4-tetrahydrocarbazole can be obtained, for example, by the action of potassium iodide on the relevant p-toluenesulfonic esters. The amines of the formula Thc-A-NH₂ are accessible, for example, from the halides using potassium phthalimide or by reduction of the corresponding nitriles.

Most of the piperidine derivatives IIIa are known (compare German Offenlegungsschrift No. 2,060,816) and can be obtained, for example, by reaction of 3- or 4-piperidone with organometallic compounds of the formula M-Ar (in which M is a Li atom or MgHal) and subsequent hydrolysis to give the corresponding 3-Ar-3- or 4-Ar-4-hydroxypiperidines, followed if desired, by dehydration to give 3-Ar- or 4-Ar3,4-dehydropiperidines and, if desired, by hydrogenation to give 3-Ar- or 4-Ar-piperidines. Compounds of the formula III ($X^2$ and $X^3$ each being X) can be prepared, for example, by reduction of 2- or 3-Ar-glutaric esters, and of 2- or 3-Ar-2-pentene-1,5-dioic esters, to 2- or 3-Ar-1,5pentanediols, and 2- or 3-Ar-2-pentene-1,5-diols respectively, and, where appropriate, subsequent reaction with SOCl₂ or PBr₃.

The reaction of the compounds II and III takes place by methods as are known from the literature for the alkylation of amines. It is possible to fuse the components together in the absence of a solvent, if appropriate in a closed tube or in an autoclave. However, it is also possible to react the compounds in the presence of an inert solvent. Examples of suitable solvents are hydrocarbons, such as benzene, toluene or xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methylpyrrolidone; nitriles, such as acetonitrile, and, if appropriate, mixtures with water. The addition of an acid-binding agent, for example an alkali metal or alkaline earth metal hydroxide, carbonate or bicarbonate or another salt of the alkali metals or alkaline earth metals, preferably of potassium, sodium or calcium, with a weak acid, or the addition of an organic base, such as triethylamine, dimethylaniline, pyridine or quinoline or an excess of the amine component Thc-A-NH₂ or of the piperidine derivative of the formula IIIa can be advantageous. Depending on the conditions used, the reaction time is between a few minutes and 14 days, and the reaction temperature is between about 0° and 150°, normally between 20° and 130°.

Furthermore, it is possible to obtain a compound of the formula I by treating a precursor, which has one or more reducible group(s) and/or one or more additional C-C and/or C-N bond(s) in place of hydrogen atoms, with reducing agents, preferably at temperatures between −80° and +250° in the presence of at least one inert solvent.

Reducible groups (which can be replaced by hydrogen) are, in particular, oxygen in a carbonyl group, hydroxyl, arylsulfonyloxy (for example p-toluenesulfonyloxy), N-benzenesulfonyl, N-benzyl or O-benzyl.

It is possible in principle to convert compounds which contain only one of the abovementioned groups or additional bonds or those compounds which contain together two or more of the abovementioned groups or additional bonds into a compound of the formula I by reduction. Nascent hydrogen or complex metal hydrides, but also reduction by the method of Wolff-Kishner, is preferably used for this purpose.

Preferred starting materials for the reduction correspond to the formula V $$\text{Thc}'—L—Q—\text{Ar}' \qquad\qquad V$$

in which Thc' is a 1,2,3,4-tetrahydro-3-carbazolyl radical which can be substituted once or twice by alkyl, O-alkyl, S-alkyl, SO-alkyl, SO₂-alkyl, OH, F, Cl, Br, CF₃, CN and/or O-benzyl or by a methylenedioxy group and/or by an arylsulfonyl group or a benzyl group in the 9-position, L is —CH₂—, —CH₂CH₂—, —CO—, —CH₂CO—, —COCH₂— or —COCO—,

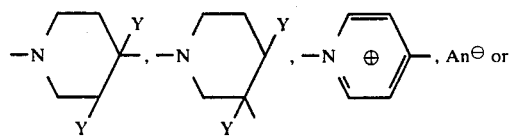

An^α is an anion of a strong acid and Ar' is a phenyl group which is unsubstituted or substituted once or twice by alkyl, O-alkyl, S-alkyl, SO-alkyl, SO₂-alkyl, OH, F, Cl, Br, CF₃, CN and/or O-benzyl or by a methylenedioxy group, or is a 2- or 3-thienyl radical, but wherein it is not possible at the same time for Thc' to be Thc, L to be A, Q to be

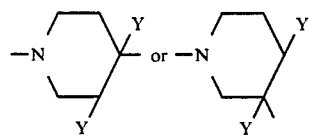

and Ar' to be Ar. L in the compounds of the formula V is preferably —CO— or —CH₂—CO—.

Compounds of the formula V can be prepared, for example, by reaction of a 3- or 4-Ar'-piperidine, -1,2,3,6-tetrahydropyridine or -pyridine with a compound of the formula VI Thc'-L-X¹   VI in which Ar', Thc', L and X¹ have the meanings indicated above, under the conditions which are indicated above for the reaction of II with III. It is possible to prepare amides of the formulae V (L=—CO— or —CH₂CO—,

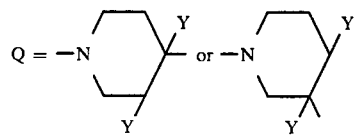

for example, from the free carboxylic acids of the formulae Thc-COOH or Thc—CH₂—COOH and piperidines of the formula IIIa in the presence of a dehydrating agent, for example carbonyldiimidazole or dicyclohexylcarbodiimide in one of the inert solvents indicated, preferably THF.

If nascent hydrogen is used as the reducing agent, this can be produced by, for example, treatment of metals with weak acids or with bases. Thus, for example, a mixture of zinc with alkali metal hydroxide solution or of iron with acetic acid can be used. It is also suitable to use sodium or another alkali metal in an alcohol, such as ethanol, isopropanol, butanol, amyl or isoamyl alcohol or phenol. It is also possible to use an aluminum/nickel alloy in an aqueous alkaline solution, optionally with the addition of ethanol. Sodium amalgam or aluminum amalgam in aqueous alcoholic or aqueous solution are also suitable to produce nascent hydrogen. The reaction can also be carried out in heterogeneous phases, it being preferable to use an aqueous and a benzene or toluene phase.

Moreover, it is possible to use with particular advantage complex metal hydrides, such as LiAlH₄, NaBH₄, diisobutylaluminum hydride or NaAl(OCH₂CH₂OCH₃)₂H₂ and diborane, as the reducing agent, if desired with the addition of catalysts, such as BF₃, AlCl₃ or LiBr. Solvents which are particularly suitable for this purpose are ethers, such as diethyl ether, di-n-butyl ether, THF, dioxane, diglyme or 1,2-dimethoxyethane, and hydrocarbons, such as benzene. For reduction with NaBH₄, alcohols, such as methanol or ethanol, but also water and aqueous alcohols, are primarily suitable as the solvent. Reduction by these methods is preferably carried out at temperatures between −80° and +150°, in particular between about 0° and about 100°.

It is possible particularly advantageously to reduce —CO— groups in amides with LiAlH₄ in THF at temperatures between about 0° and 66° to give CH₂ groups. During this, arylsulfonyl protective groups located in the 9-position of the 1,2,3,4-tetrahydrocarbazole ring can simultaneously be reductively split off.

It is possible to reduce the pyridinium salts of the formula V (in which Q is

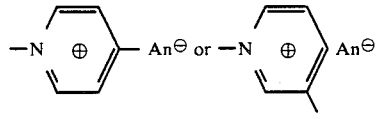

and An⊖ is preferably Cl or Br, to give compounds of the formula I, for example using NaBH₄ in water, methanol or ethanol or in mixtures of these solvents, with the addition, if desired, of a base, such as NaOH, at temperatures between about 0° and 80°.

N-Benzyl groups can be reductively split off using sodium in liquid ammonia.

Moreover, it is possible to reduce one or more carbonyl groups to CH₂ groups by the method of Wolff-Kishner, for example by treatment with anhydrous hydrazine in absolute ethanol under pressure at temperatures between about 150° and 250°. Sodium alcoholate is advantageously used as a catalyst. The reduction can also be modified by the method of Huang-Minlon by carrying out the reaction with hydrazine hydrate in a high-boiling solvent which is miscible with water, such as diethylene glycol or triethylene glycol, in the presence of alkali, such as sodium hydroxide. As a rule, the reaction mixture is boiled for about 3–4 hours. The water is then distilled off and the hydrazone formed is decomposed at temperatures up to about 200°. The Wolff-Kishner reduction can also be carried out with hydrazine in dimethyl sulfoxide at room temperature.

Compounds which otherwise correspond to formula I but, in place of one or more H atoms, contain one or more group(s) which can be split off by solvolysis can be solvolyzed, in particular hydrolyzed, to give compounds of the formula I. The starting materials for the solvolysis can be obtained, for example, by reaction of IIIa with compounds which correspond to the formula II ($X^1$=X) but which contain, in place of one or more H atoms, one or more group(s) which can be split off by solvolysis. Thus, 1-acyl-1,2,3,4-tetrahydrocarbazole derivatives (corresponding to the formula I but containing an acyl group, preferably an alkanoyl, alkylsulfonyl or arylsulfonyl group, each having up to 10 C atoms, such as methane-, benzene- or p-toluene-sulfonyl, in the 9-position of the Thc radical) can be hydrolyzed to give the corresponding 1,2,3,4-tetrahydrocarbazole derivatives which are unsubstituted in the 1-position of the 1,2,3,4-tetrahydrocarbazole ring, for example in acid, but better in neutral or alkaline medium at temperatures between 0° and 200°. Sodium, potassium or calcium hydroxide, sodium or potassium carbonate or ammonia are preferably used as the basic catalysts. The solvents which are preferably chosen are water, lower alcohols, such as methanol or ethanol, ethers, such as THF or dioxane, sulfones, such as tetramethylenesulfone, or their mixtures. Hydrolysis can even take place just on treatment with water alone, in particular at the boiling point.

Moreover, the compounds of the formula I in which the two radicals Y are together a C-C bond are also accessible by eliminating HE from compounds of the formula IV with the formation of a double bond. Depending on the definition of E, this can be, for example, elimination of hydrogen halide, water (dehydration), a carboxylic acid or another acid, of ammonia or of HCN. The starting materials of the formula IV can be obtained, for example, by reaction of II ($X^1$=X) with a compound of the formula IX

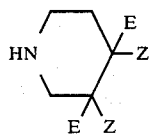

IX in which E and Z have the meanings indicated.

If one of the radicals E is Hal, this substituent can easily be eliminated under basic reaction conditions. The following can be used as bases: alkali metal hydroxides, alkali metal carbonates, alcoholates, such as, for example, potassium tert.-butylate, amines, such as, for example, dimethylaniline, pyridine, collidine or quinoline; the solvent used is, for example, benzene, toluene, cyclohexane, methanol, dioxane, THF or tert.-butanol. The amines used as bases can also be employed in excess as the solvent. If one of the radicals E is an OH group, then acids, such as acetic acid, hydrochloric acid or mixtures of the two, are preferably used as the agent to eliminate water. The addition of a solvent (for example water or ethanol) can be advantageous. The elimination of acyl, alkylsulfonyl and alkoxysulfonyloxy or amino radicals can be carried out under similar conditions. An elimination of sulfonic acid radicals, for example mesylates or tosylates, takes place under mild conditions by boiling in DMF or dimethyl sulfoxide with alkali metal carbonates, for example $Li_2CO_3$, or with potassium acetate. Ammonia can be eliminated by just heating the salts of the corresponding amino compounds (especially the 4-amino derivatives). In a similar manner, HCN can be eliminated from compounds of the formula IV (one group E=CN) by heating. The elimination of HE from IV generally takes place at temperatures between about 0° and about 250°, preferably between 50° and 200°.

Furthermore, the thioether group in a thioether of the formula I can be oxidized to a SO group or to a $SO_2$ group, or the SO group in a sulfoxide of the formula I can be oxidized to a $SO_2$ group. The thioether or sulfoxide groups to be oxidized can be present as substituents in the radical Thc and/or in the radical Ar. If the intention is to obtain the sulfoxides, then the oxidation is carried out with, for example, hydrogen peroxide, peracids, such as m-chloroperbenzoic acid, Cr(VI) compounds, such as chromic acid, $KMnO_4$, 1-chlorobenzotriazole, Ce(IV) compounds, such as $(NH_4)_2Ce(NO_3)_6$, negative substituted aromatic diazonium salts, such as o- or p-nitrophenyldiazonium chloride, or electrolytically under relatively mild conditions and at relatively low temperatures (about $-80°$ to 100°) If, on the other hand, the intention is to obtain the sulfones (from the thioethers or the sulfoxides), then the same oxidizing agents are used under more forcing conditions and/or in excess and, as a rule, at higher temperatures. It is possible in these reactions for the customary inert solvents to be present or absent. Examples of suitable inert solvents are water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, chlorinated hydrocarbons, such as chloroform or $CCl_4$. A preferred oxidizing agent is 30% aqueous hydrogen peroxide. On using the calculated amount in solvents such as acetic acid, acetone, methanol, ethanol or aqueous sodium hydroxide solution at temperatures between $-20°$ and 100°, this leads to the sulfoxides, while in excess at higher temperatures, preferably in acetic acid or in a mixture of acetic acid and acetic anhydride, this leads to the sulfones.

Ethers of the formula I in which the radicals Thc and/or Ar are substituted once or twice by O-alkyl can be cleaved by methods known from the literature, the corresponding hydroxy derivatives being produced. For example, the ethers can be cleaved by treatment with HBr or HI in aqueous or acetic acid solution, by heating with Lewis acids, such as $AlCl_3$ or boron trihalides, or by fusing with pyridine or aniline hydrohalides, preferably pyridine hydrochloride, at about 150°–250°. Reductive cleavage using diisobutylaluminium hydride (for method, compare Synthesis 1975, 617) is particularly mild.

If desired, unsaturated compounds of the formula I in which the two radicals Y are together a C-C bond can be hydrogenated to give the corresponding saturated compounds of the formula I in which the two radicals Y are each H, preferably in the presence of a heavy metal catalyst, such as platinum, palladium or Raney nickel, in an inert solvent, for example an alcohol such as methanol or ethanol, at temperatures between about 0° and 150°, and under pressures between about 1 and 200 bar.

A base of the formula I which has been obtained can be converted into the relevant acid addition salt using an acid. Acids which provide physiologically acceptable salts are suitable for this reaction. Thus, inorganic acids can be used, for example sulfuric acid, hydrohalic acids, such as hydrochloric acid or hydrobromic acid, phosphoric acids, such as orthophosphoric acid, nitric acid or sulfamic acid, but also organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids, and laurylsulfuric acid.

It is possible, if desired, to liberate the free bases of the formula I from their salts by treatment with strong bases, such as sodium or potassium hydroxide or sodium or potassium carbonate.

The invention also relates to the use of the compounds of the formula I and their physiologically acceptable salts for the preparation of pharmaceutical formulations, in particular by non-chemical means. For this purpose, it is possible to convert them into a suitable form for administration together with at least one vehicle or auxiliary and, where appropriate, combined with one or more other active compound(s).

The invention also relates to agents, especially pharmaceutical formulations, containing at least one compound of the formula I and/or one of its physiologically acceptable salts. These formulations can be employed as medicaments in human or veterinary medicine. Suitable vehicles are organic or inorganic substances which are suitable for enteral (for example oral), parenteral or topical administration and which do not react with the new compounds, for example water, vegetable oils, benzyl alcohols, polyethylene glycols, gelatine, carbohydrates, such as lactose or starch, magnesium stearate, talc and vaseline. In particular, tablets, coated tablets, capsules, syrups, liquids, drops or suppositories are used for enteral administration, solutions, preferably oily or aqueous solutions, but also suspensions, emulsions or implants are used for parenteral administration, and ointments, creams or powders are used for topical application. It is also possible to freeze-dry the new compouqds and use the lyophilizates obtained, for example for the preparation of products for injection.

The indicated formulations can be sterilized and/or contain auxiliaries, such as lubricants, preservatives, stabilizers and/or wetting agents, emulsifiers, salts to modify the osmotic pressure, buffer substances, colorants, flavorings and/or aromatic substances. If desired, they can also contain one or more other active compounds, for example one or more vitamins.

The invention also relates to the use of the compounds of the formula I and their physiologically acceptable salts for the therapeutic treatment of the human or animal body and for the control of illnesses, especially of parkinsonism, of extrapyramidal disturbances associated with neuroleptic therapy, of depression and/or psychosis and of side effects of treatment for hypertension (for example with α-methyldopa). The compounds can also be used in endocrinology and gynaecology, for example for the therapy of acromegaly, hypogonadism, secondary amenorrhoea, premenstrual syndrome, undesired puerperal lactation and generally as prolactin inhibitors, also for the therapy of cerebral disturbances (for example migraine) and especially in geriatrics, similarly to certain ergot alkaloids.

For these purposes, as a rule the substances according to the invention are administered in analogy to known and commercially available products (for example bromocriptine and dihydroergocornine), preferably in doses between about 0.2 and 500 mg, in particular between 0.2 and 50 mg per dosage unit. The daily dose is preferably between about 0.001 and 10 mg/kg of body weight. In this context, the low doses (about 0.2 to 1 mg per dosage unit; about 0.001 to 0.005 mg/kg of body weight) are particularly suitable for use as agents for migraine; doses between 10 and 50 mg per dosage unit are preferred for the other indications. Preferred dose ranges for specific indications are as follows: parkinsonism 1 to 200, preferably 40 to 100; dyskinesia 40 to 100; psychosis, for example schizophrenia, 2 to 20; acromegaly 2 to 50 mg per dosage unit. However, the specific dose for each particular patient depends on a wide variety of factors, for example on the efficacy of the specific compound employed, on the age, body weight, general state of health, sex, on the diet, on the timing and mode of administration, on the rate of excretion, and on medicaments used in combination and the severity of the particular disorder to which the therapy is applied. Oral administration is preferred.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merley illustrative, and not limitative of the remainder of the disclosure in any way whatsoever. In the following examples, all temperatures are set forth uncorrected in degrees Celsius; unless otherwise indicated, all parts and percentages are by weight.

In the examples below, "usual work-up" denotes:

Water is added if necessary, the mixture is extracted with an orqanic solvent, such as toluene, chloroform or dichloromethane, the phases are separated, the organic phase is dried over sodium sulfate, filtered and evaporated and the product is purified by chromatography and/or crystallization. Temperatures are reported in degrees centigrade. Rf values on silica gel ($CH_2Cl_2$/methanol 95:5 unless otherwise indicated).

EXAMPLE 1

A solution of 2.19 g of 3-chloromethyl-1,2,3,4-tetrahydrocarbazole (or 2.63 g of 3-bromomethyl-1,2,3,4-tetrahydrocarbazole) (obtainable by reduction of 1,2,3,4-tetrahydrocarbazole-3-carboxylic acid with $LiAlH_4$ to give 3-hydroxymethyl-1,2,3,4-tetrahydrocarbazole, followed by reaction with $SOCl_2$ or $PBr_3$) and 1.6 g of 4-phenyl-1,2,3,6-tetrahydropyridine in 10 ml of acetonitrile is stirred at 20° for 12 hours, worked up as usual and 3-(4-phenyl-1,2,3,6-tetrahydro-1-pyridylmethyl)1,2,3,4-tetrahydrocarbazole ("P") is obtained. M.p. 163°–65°.

In analogy, from the appropriate 3-chloroalkyl- or 3-bromoalkyl-1,2,3,4-tetrahydrocarbazoles, for example 3-chloromethyl-6-methoxy-1,2,3,4-tetrahydrocarbazole, 3-chloromethyl-7-methoxy-1,2,3,4-tetrahydrocarbazole, 3-chloromethyl-6-hydroxy-1,2,3,4-tetrahydrocarbazole, 3-chloromethyl-7-hydroxy-1,2,3,4-tetrahydrocarbazole, 3-chloromethyl-6,7-dimethoxy-1,2,3,4-tetrahydrocarbazole, 3-(2-chloroethyl)-1,2,3,4-tetrahydrocarbazole, 3-(2-chloroethyl)-6-methoxy-1,2,3,4-tetrahydrocarbazole, 3-(2-chloroethyl)-7-methoxy-1,2,3,4-tetrahydrocarbazole, 3-(2-chloroethyl)-6-hydroxy-1,2,3,4-tetrahydrocarbazole, 3-(2-chloroethyl)-7-hydroxy-1,2,3,4-tetrahydrocarbazole, 3-(2-chloroethyl)-7-chloro-1,2,3,4-tetrahydrocarbazole or 3-(2-chloroethyl)-6,7-dimethoxy-1,2,3,4-tetrahydrocarbazole, with the appropriate 4-aryl-1,2,3,6-tetrahydropyridines, the following are obtained:

3-(4-phenyl-1,2,3,6-tetrahydro-1-pyridylmethyl)-6-methyl-1,2,3,4-tetrahydrocarbazole, 3-(4-phenyl-1,2,3,6-tetrahydro-1-pyridylmethyl)-7-methyl-1,2,3,4-tetrahydrocarbazole, 3-(4-phenyl-1,2,3,6-tetrahydro-1-pyridylmethyl)-9-methyl-1,2,3,4-tetrahydrocarbazole, 3-(4-phenyl-1,2,3,6-tetrahydro-1-pyridylmethyl)-6-methoxy-1,2,3,4-tetrahydrocarbazole, m.p. 161°-163°, 3-(4-phenyl-1,2,3,6-tetrahydro-1-pyridylmethyl)-7-methoxy-1,2,3,4-tetrahydrocarbazole, m.p. 164°-166°

3-(4-phenyl-1,2,3,6-tetrahydro-1-pyridylmethyl)-8-methoxy-1,2,3,4-tetrahydrocarbazole, 3-(4-phenyl-1,2,3,6-tetrahydro-1-pyridylmethyl)-6-ethoxy-1,2,3,4-tetrahydrocarbazole, 3-(4-phenyl-1,2,3,6-tetrahydro-1-pyridylmethyl)-6-methylthio-1,2,3,4-tetrahydrocarbazole, 3-(4-phenyl-1,2,3,6-tetrahydro-1-pyridylmethyl)-7-methylthio-1,2,3,4-tetrahydrocarbazole, 3-(4-phenyl-1,2,3,6-tetrahydro-1-pyridylmethyl)-6-methylsulfinyl-1,2,3,4-tetrahydrocarbazole, 3-(4-phenyl-1,2,3,6-tetrahydro-1-pyridylmethyl)-7-methylsulfinyl-1,2,3,4-tetrahydrocarbazole, 3-(4-phenyl-1,2,3,6-tetrahydro-1-pyridylmethyl)-6-methylsulfonyl-1,2,3,4-tetrahydrocarbazole, 3-(4-phenyl-1,2,3,6-tetrahydro-1-pyridylmethyl)-7-methylsulfonyl-1,2,3,4-tetrahydrocarbazole, 3-(4-phenyl-1,2,3,6-tetrahydro-1-pyridylmethyl)-5-hydroxy-1,2,3,4-tetrahydrocarbazole, 3-(4-phenyl-1,2,3,6-tetrahydro-1-pyridylmethyl)-6-hydroxy-1,2,3,4-tetrahydrocarbazole, Rf 0.2 (toluene/triethylamine 9:1), 3-(4-phenyl-1,2,3,6-tetrahydro-1-pyridylmethyl)-7-hydroxy-1,2,3,4-tetrahydrocarbazole, Rf 0.28 ($CH_2Cl_2$methanol 9:1)

3-(4-phenyl-1,2,3,6-tetrahydro-1-pyridylmethyl)-8-hydroxy-1,2,3,4-tetrahydrocarbazole, 3-(4-phenyl-1,2,3,6-tetrahydro-1-pyridylmethyl)-6-fluoro-1,2,3,4-tetrahydrocarbazole, 3-(4-phenyl-1,2,3,6-tetrahydro-1-pyridylmethyl)-7-fluoro-1,2,3,4-tetrahydrocarbazole, 3-(4-phenyl-1,2,3,6-tetrahydro-1-pyridylmethyl)-6-chloro-1,2,3,4-tetrahydrocarbazole, 3-(4-phenyl-1,2,3,6-tetrahydro-1-pyridylmethyl)-7-chloro-1,2,3,4-tetrahydrocarbazole, 3-(4-phenyl-1,2,3,6-tetrahydro-1-pyridylmethyl)-6-bromo-1,2,3,4-tetrahydrocarbazole, 3-(4-phenyl-1,2,3,6-tetrahydro-1-pyridylmethyl)-7-bromo-1,2,3,4-tetrahydrocarbazole, 3-(4-phenyl-1,2,3,6-tetrahydro-1-pyridylmethyl)-6-trifluoromethyl-1,2,3,4-tetrahydrocarbazole, 3-(4-phenyl-1,2,3,6-tetrahydro-1-pyridylmethyl)-7-trifluoromethyl-1,2,3,4-tetrahydrocarbazole, 3-(4-phenyl-1,2,3,6-tetrahydro-1-pyridylmethyl)-6-cyano-1,2,3,4-tetrahydrocarbazole, 3-(4-phenyl-1,2,3,6-tetrahydro-1-pyridylmethyl)-7-cyano-1,2,3,4-tetrahydrocarbazole, 3-(4-phenyl-1,2,3,6-tetrahydro-1-pyridylmethyl)-8-cyano-1,2,3,4-tetrahydrocarbazole, 3-(4-phenyl-1,2,3,6-tetrahydro-1-pyridylmethyl)-6,7-dimethoxy-1,2,3,4-tetrahydrocarbazole, m.p. 178°-180°, methylenedioxy-1,2,3,4-tetrahydrocarbazole, 3-(4-o-tolyl-1,2,3,6-tetrahydro-1-pyridylmethyl)-1,2,3,4-tetrahydrocarbazole, 3-(4-m-tolyl-1,2,3,6-tetrahydro-1-pyridylmethyl)-1,2,3,4-tetrahydrocarbazole, 3-(4-p-tolyl-1,2,3,6-tetrahydro-1-pyridylmethyl)-1,2,3,4-tetrahydrocarbazole, 3-(4-o-methoxyphenyl-1,2,3,6-tetrahydro-1-pyridylmethyl)-1,2,3,4-tetrahydrocarbazole, 3-(4-m-methoxyphenyl-1,2,3,6-tetrahydro-1-pyridylmethyl)-1,2,3,4-tetrahydrocarbazole, 3-(4-p-methoxyphenyl-1,2,3,6-tetrahydro-1-pyridylmethyl)-2,3,4-tetrahydrocarbazole, 3-(4-o-hydroxyphenyl-1,2,3,6-tetrahydro-1-pyridylmethyl)-1,2,3,4-tetrahydrocarbazole, 3-(4-m-hydroxyphenyl-1,2,3,6-tetrahydro-1-pyridylmethyl)-1,2,3,4-tetrahydrocarbazole, 3-(4-p-hydroxyphenyl-1,2,3,6-tetrahydro-1-pyridylmethyl)-1,2,3,4-tetrahydrocarbazole, 3-(4-o-fluorophenyl-1,2,3,6-tetrahydro-1-pyridylmethyl)-1,2,3,4-tetrahydrocarbazole, 3-(4-m-fluorophenyl-1,2,3,6-tetrahydro-1-pyridylmethyl)-1,2,3,4-tetrahydrocazole, 3-(4-p-fluorophenyl-1,2,3,6-tetrahydro-1-pyridylmethyl)-1,2,3,4-tetrahydrocarbazole, 3-(4-o-chlorophenyl-1,2,3,6-tetrahydro-1-pyridylmethyl)-1,2,3,4-tetrahydrocarbazole, 3-(4-m-chlorophenyl-1,2,3,6-tetrahydro-1-pyridylmethyl)-1,2,3,4-tetrahydrocarbazole, 3-(4-p-chlorophenyl-1,2,3,6-tetrahydro-1-pyridylmethyl)-1,2,3,4-tetrahydrocarbazole, 3-(4-p-bromophenyl-1,2,3,6-tetrahydro-1-pyridylmethyl)-1,2,3,4-tetrahydrocarbazole, 3-(4-m-trifluoromethylphenyl-1,2,3,6-tetrahydro-1-pyridylmethyl)-1,2,3,4-tetrahydrocarbazole, 3-(4-p-cyanophenyl-1,2,3,6-tetrahydro-1-pyridylmethyl)-1,2,3,4-tetrahydrocarbazole, 3-[4-(3,4-dimethoxyphenyl)-1,2,3,6-tetrahydro-1-pyridylmethyl]-1,2,3,4-tetrahydrocarbazole, 3-[4-(3,4-methylenedioxyphenyl)-1,2,3,6-tetrahydro-1pyridylmethyl]-1,2,3,4-tetrahydrocarbazole, 3-[4-(4-chloro-3-trifluoromethylphenyl)-1,2,3,6-tetrahydro-1-pyridylmethyl]-1,2,3,4-tetrahydrocarbazole, 3-[2-(4-phenyl-1,2,3,6-tetrahydropyridyl)ethyl]-1,2,3,4tetrahydrocarbazole, hydrochloride, m.p. 263°-265°, 3-[2-(4-phenyl-1,2,3,6-tetrahydropyridyl)ethyl]-6-methyl-1,2,3,4-tetrahydrocarbazole, 3-[2-(4-phenyl-1,2,3,-tetrahydropyridyl)ethyl]-6-methoxy-1,2,3,4-tetrahydrocarbazole, hydrochloride, m.p. 214°-216°, 3-[2-(4-phenyl-1,2,3,6-tetrahydropyridyl)ethyl]-7-methoxy-1,2,3,4-tetrahydrocarbazole, hydrochloride, m.p. 258°-260°, 3-[2-(4-phenyl-1,2,3,6-tetrahydropyridyl)ethyl]-6-methy-1,2,3,4-tetrahydrocarbazolethiole 3-[2-(4-phenyl-1,2,3,6-tetrahydropyridyl)ethyl]-7-methylthio-1,2,3,4-tetrahydrocarbazole, 3-[2-(4-phenyl-1,2,3,6-tetrahydropyridyl)ethyl]-5hydoxy-1,2,3,4-tetrahydrocarbazole,
3-[2-(4-phenyl-1,2,3,6-tetrahydropyridyl)ethyl]-6-hydroxy-1,2,3,4-tetrahydrocarbazole, hydrochloride, m.p. 290°–292°,
3-[2-(4-phenyl-1,2,3,6-tetrahydropyridyl)ethyl]-7-hydroxy-1,2,3,4-tetrahydrocarbazole, m.p. 206°–208°
3-[2-(4-phenyl-1,2,3,6-tetrahydropyridyl)ethyl]-8-hydroxy-1,2,3,4-tetrahydrocarbazole,
3-[2-(4-phenyl-1,2,3,6-tetrahydropyridyl)ethyl]-6-fluoro-1,2,3,4-tetrahydrocarbazole,
3-[2-(4-phenyl-1,2,3,6-tetrahydropyridyl)ethyl]-7-fluoro-1,2,3,4-tetrahydrocarbazole,
3-[2-(4-phenyl-1,2,3,6-tetrahydropyridyl)ethyl]-6-chloro-1,2,3,4-tetrahydrocarbazole,
3-[2-(4-phenyl-1,2,3,6-tetrahydropyridyl)ethyl]-7-chloro-1,2,3,4-tetrahydrocarbazole, m.p. 182-184o,
3-[2-(4-phenyl-1,2,3,6-tetrahydropyridyl)ethyl]-6-bromo-1,2,3,4-tetrahydrocarbazole,
3-[2-(4-phenyl-1,2,3,6-tetrahydropyridyl)ethyl]-7-bromo-1,2,3,4-tetrahydrocarbazole,
3-[2-(4-phenyl-1,2,3,6-tetrahydropyridyl)ethyl]-6-trifluoromethyl-1,2,3,4-tetrahydrocarbazole,
3-[2-(4-phenyl-1,2,3,6-tetrahydropyridyl)ethyl]-7-trifluoromethyl-1,2,3,4-tetrahydrocarbazole,
3-[2-(4-phenyl-1,2,3,6-tetrahydropyridyl)ethyl]-6-cyano-1,2,3,4-tetrahydrocarbazole,
3-[2-(4-phenyl-1,2,3,6-tetrahydropyridyl)ethyl]-7-cyano-1,2,3,4-tetrahydrocarbazole,
3-[2-(4-phenyl-1,2,3,6-tetrahydropyridyl)ethyl]-8-cyano-1,2,3,4-tetrahydrocarbazole,
3-[2-(4-phenyl-1,2,3,6-tetrahydropyridyl)ethyl]-6,7-dimethoxy-1,2,3,4-tetrahydrocarbazole, hydrochloride, m.p. 172°–174°, or
3-[2-(4-phenyl-1,2,3,6-tetrahydropyridyl)ethyl]-6,7-methylenedioxy-1,2,3,4-tetrahydrocarbazole.

EXAMPLE 2

A mixture of 4.54 g of 3-p-toluenesulfonyloxymethyl-1,2,3,4-tetrahydrocarbazole and 3.18 g of 4- phenyl-1,2,3,6-tetrahydropyridine is heated at 130°. After the exothermic reaction has subsided and the mixture has cooled, it is worked up as usual and "P" of m.p. 163°–165° is obtained.

In analogy, the following are obtained from the appropriate tosylates:
3-(4-phenyl-1,2,3,6-tetrahydro-1-pyridylmethyl)-1-methyl-1,2,3,4-tetrahydrocarbazole,
3-(4-phenyl-1,2,3,6-tetrahydro-1-pyridylmethyl)-2-methyl-1,2,3,4-tetrahydrocarbazole,
3-(4-phenyl-1,2,3,6-tetrahydro-1-pyridylmethyl)-3-methyl-1,2,3,4-tetrahydrocarbazole,
3-(4-phenyl-1,2,3,6-tetrahydro-1-pyridylmethyl)-4-methyl-1,2,3,4-tetrahydrocarbazole,
3-(4-phenyl-1,2,3,6-tetrahydro-1-pyridylmethyl)-6-butyl-1,2,3,4-tetrahydrocarbazole,
3-(4-phenyl-1,2,3,6-tetrahydro-1-pyridylmethyl)-6-butoxy-1,2,3,4-tetrahydrocarbazole and
3-(4-phenyl-1,2,3,6-tetrahydro-1-pyridylmethyl)-6-butylthio-1,2,3,4-tetrahydrocarbazole.

EXAMPLE 3

3.1 g of 3-iodomethyl-1,2,3,4-tetrahydrocarbazole, 1.59 g of 4-phenyl-1,2,3,6-tetrahydropyridine and 1.5 g of anhydrous potassium carbonate in 25 ml of n-butanol are boiled with stirring for 2 hours, allowed to cool, worked up as usual and "P" of m.p. 163°–165° is obtained.

In analogy, the following are obtained using the appropriate 4-Ar-1,2,3,6-tetrahydropyridines:
3-(4-p-butoxyphenyl-1,2,3,6-tetrahydro-1-pyridylmethyl)-1,2,3,4-tetrahydrocarbazole,
3-(4-p-methylthiophenyl-1,2,3,6-tetrahydro-1-pyridylmethyl)-1,2,3,4-tetrahydrocarbazole,
3-(4-p-butylthiophenyl-1,2,3,6-tetrahydro-1-pyridylmethyl)-1,2,3,4-tetrahydrocarbazole,
3-(4-p-methylsulfinylphenyl-1,2,3,6-tetrahydro-1-pyridylmethyl)-1,2,3,4-tetrahydrocarbazole and
3-(4-p-methylsulfonylphenyl-1,2,3,6-tetrahydro-1-pyridylmethyl)-1,2,3,4-tetrahydrocarbazole.

EXAMPLE 4

A mixture of 2.0 g of 3-aminomethyl-1,2,3,4-tetrahydrocarbazole (obtainable by reaction of 3-bromomethyl-1,2,3,4-tetrahydrocarbazole with potassium phthalimide followed by hydrolysis) and 2.15 g of 1,5-dichloro-3-phenyl-2-pentene (obtainable by reduction of diethyl 3-phenyl-2-pentene-1,5-dioate with LiAlH$_4$ followed by reactfon with SOCl$_2$) in 40 ml of acetone and 40 ml of water is boiled for 24 hours and worked up as usual. "P" of m.p. 163°–165° is obtained.

In analogy, the other compounds of the formula I indicated in Examples 1, 2 and 3 are obtained from the appropriate amines and the appropriate 1,5-dichloro-3-Ar-2-pentenes.

EXAMPLE 5

1 g of NaBH$_4$ in 20 ml of water is added, with stirring, to a solution of 4.19 g of 1-(1,2,3,4-tetrahydro-3-carbazolylmethyl)-4-phenylpyridinium bromide (obtainable from 3-bromomethyl-1,2,3,4-tetrahydrocarbazole and 4-phenylpyridine) in 50 ml of 1N NaOH, and the mixture is then stirred at 60° for 3 hours. After the usual work-up, "P" of m.p. 163°–165° is obtained.

In analogy, the other compounds of the formula I indicated in Examples 1, 2 and 3 are obtained by reduction of the appropriate pyridinium bromides.

EXAMPLE 6

A solution of 3.56 g of 3-(4-phenyl-1,2,3,6-tetrahydropyridylcarbonyl)-1,2,3,4-tetrahydrocarbazole (Rf 0.9; obtainable from 1,2,3,4-tetrahydrocarbazole-3carboxylic acid and 4-phenyl-1,2,3,6-tetrahydropyridine in the presence of carbonyldiimidazole in THF at 20°) in 10 ml of THF is added dropwise, with stirring, to a suspension of 0.3g of LiAlH$_4$ in 10 ml of THF. After the reaction has subsided, 5 ml of ethyl acetate are added, the mixture is worked up as usual and "P" of m.p. 163°–165° is obtained.

In analogy, from the appropriate amides, for example:
3-(4-phenyl-1,2,3,6-tetrahydropyridylcarbonyl)-6-methoxy-1,2,3,4-tetrahydrocarbazole (m.p. 210°–212°),
3-(4-phenyl-1,2,3,6-tetrahydropyridylcarbonyl)-7-methoxy-1,2,3,4-tetrahydrocarbazole (Rf 0.2, CH$_2$Cl$_{12}$/methanol 98:2)
3-(4-phenyl-1,2,3,6-tetrahydropyridylcarbonyl)-6-hydroxy-1,2,3,4-tetrahydrocarbazole (m.p. 210-212o),
3-(4-phenyl-1,2,3,6-tetrahydropyridylcarbonyl)-6,7-dimethoxy-1,2,3,4-tetrahydrocarbazole (m.p. 143°–145°),
3-(4-phenyl-1,2,3,6-tetrahydropyridylcarbonylmethyl-)e1,2,3,4-tetrahydrocarbazole (Rf 0.8, toluene/CH$_3$OH/triethylamine 7:2:1), 3-(4-phenyl-1,2,3,6-tetrahydropyridylcarbonylmethyl)-6-methoxy-1,2,3,4-tetrahydrocarbazole (Rf 0.85),
3-(4-phenyl-1,2,3,6-tetrahydropyridylcarbonylmethyl)-7-methoxy-1,2,3,4-tetrahydrocarbazole (Rf 0.6),
3-(4-phenyl-1,2,3,6-tetrahydropyridylcarbonylmethyl)-6-hydroxy-1,2,3,4-tetrahydrocarbazole (Rf 0.85),
3-(4-phenyl-1,2,3,6-tetrahydropyridylcarbonylmethyl)-7-chloro-1,2,3,4-tetrahydrocarbazole (Rf 0.9) and
3-(4-phenyl-1,2,3,6-tetrahydropyridylcarbonylmethyl)-6,7-dimethoxy-1,2,3,4-tetrahydrocarbazole (Rf 0.85), the other compounds of the formula I indicated in Examples 1 to 3 are obtained.

EXAMPLE 7

4.82 g of 9-benzenesulfonyl-3-(4-phenyl-1,2,3,6-tetrahydropyridylmethyl)-1,2,3,4-tetrahydrocarbazole (obtainable from 9-benzenesulfonyl-3-chloromethyl-1,2,3,4-tetrahydrocarbazole and 4-phenyl-1,2,3,6-tetrahydropyridine) are boiled with 1 g of KOH in 7 ml of water and 14 ml of ethanol for 16 hours, the mixture is concentrated, worked up as usual and "P" of m.p. 163°–165° is obtained.

EXAMPLE 8

3.74 g of 3-(4-hydroxy-4-phenyl-1-piperidylmethyl)-9-methyl-1,2,3,4-tetrahydrocarbazole (obtainable by reaction of 3-bromomethyl-9-methyl-1,2,3,4-tetrahydrocarbazole with 4-piperidone followed by reaction with $C_6H_5Li$ and hydrolysis) are heated with 40 ml of 1N hydrochloric acid at 50° for 2 hours, the mixture is worked up as usual and 3-(4-phenyl-1,2,3,6-tetrahydropyridylmethyl)-9-methyl-1,2,3,4-tetrahydrocarbazole is obtained.

EXAMPLE 9

6 ml of 30% $H_2O_2$ are added to a boiling solution of 3.88 g of 3-(4-phenyl-1,2,3,6-tetrahydro-1-pyridylmethyl)-7-methylthio-1,2,3,4-tetrahydrocarbazole in 50 ml of ethanol and the mixture is then boiled for 3 hours. After addition of a further 4 ml of the oxidizing agent, the mixture is boiled for 9 hours, cooled, worked up as usual and 3-(4-phenyl-1,2,3,6-tetrahydro-1-pyridylmethyl)-7-methylsulfinyl-1,2,3,4-tetrahydrocarbazole is obtained.

EXAMPLE 10

9 ml of 30% $H_2O_2$ are added to a solution of 3.88 g of 3-(4-phenyl-1,2,3,6-tetrahydro-1-pyridylmethyl)-7-methylthio-1,2,3,4-tetrahydrocarbazole in 20 ml of acetic acid and the mixture is boiled for 90 minutes. After the usual work-up, 3-(4-phenyl-1,2,3,6-tetrahydro-1-pyridylmethyl)-7-methylsulfonyl-1,2,3,4-tetrahydrocarbazole is obtained.

EXAMPLE 11

A mixture of 4.19 g of 3-(4-phenyl-1,2,3,6-tetrahydro-1-pyridylmethyl)-6-methoxy-1,2,3,4-tetrahydrocarbazole hydrochloride and 3.5 g of pyridine hydrochloride is stirred at 160° for 3 hours. After the usual work-up, 3-(4-phenyl-1,2,3,6-tetrahydro-1-pyridylmethyl)-6-hydroxy-1,2,3,4-tetrahydrocarbazole, Rf 0.2 (toluene/triethylamine 9:1), is obtained.

EXAMPLE 12

In analogy to example 6, the following are obtained from the appropriate amides:
3-[4-(2-thienyl)-1,2,3,6-tetrahydro-1-pyridylmethyl]-1,2,3,4-tetrahydrocarbazole
3-(4-phenylpiperidinomethyl)-1,2,3,4-tetrahydrocarbazole-3-(4-phenylpiperidinomethyl)-6-hydroxy-1,2,3,4-tetrahydrocarbazole
3-(4-phenylpiperidinomethyl)-7-hydroxy-1,2,3,4-tetrahydrocarbazole
3-(4-m-methoxyphenylpiperidinomethyl)-1,2,3,4-tetrahydrocarbazole
3-(4-m-hydroxyphenylpiperidinomethyl)-1,2,3,4-tetrahydrocarbazole
3-(3-phenyl-1,2,5,6-tetrahydro-1-pyridylmethyl)-1,2,3,4-tetrahydrocarbazole
3-(3-.phenyl-1,2,5,6-tetrahydro-1-pyridylmethyl)-6-hydroxy-1,2,3,4-tetrahydrocarbazole-(3-phenyl-1,2,5,6-tetrahydro-1-pyridylmethyl)-7-hydroxy-1,2,3,4-tetrahydrocarbazole
3-(3-m-methoxyphenyl-1,2,5,6-tetrahydro-1-pyridylmethyl)-1,2,3,4-tetrahydrocarbazole
3-(3-m-hydroxyphenyl-1,2,5,6-tetrahydro-1-pyridylmethyl)-1,2,3,4-tetrahydrocarbazole
3-(3-phenylpiperidinomethyl)-1,2,3,4-tetrahydrocarbazole-(3-phenylpiperidinomethyl)-6-hydroxy-1,2,3,4-tetrahydrocarbazole
3-(3-phenylpiperidinomethyl)-7-hydroxy-1,2,3,4-tetrahydrocarbazole
3-(3-m-methoxyphenylpiperidinomethyl)-1,2,3,4-tetrahydrocarbazole, Rf 0.65 ($Ch_2Cl_2$/methanol 9:1)
3-(3-m-methoxyphenylpiperidinomethyl)-6-methoxy-1,2,3,4-tetrahydrocarbazole, Rf 0.7 ($CH_2Cl_2$/methanol 9:1)
3-(3-m-hydroxyphenylpiperidinomethyl)-1,2,3,4-tetrahydrocarbazole, m.p. 128°–130°
3-(3-m-hydroxyphenylpiperidinomethyl)-6-hydroxy-1,2,3,4tetrahydrocarbazole, m.p. 123°–125°.

EXAMPLE 13

A solution of 1 g of 3-(3-m-hydroxyphenol-1,2,5,6-tetrahydro-1-pyridylmethyl)-1,2,3,4-tetrahydrocarbazole in 15 ml of methanol is hydrogenated in 1 g of 5% Pd-C under 1 bar and at 20° C. The mixture is filtered, evaporated, and 3-(3-m-hydroxyphenyl-piperidinomethyl)-1,2,3,4-tetrahydrocarbazole, m.p. 128°–130°, is obtained.

The examples which follow relate to pharmaceutical formulations which contain amines of the formula I or their acid addition salts:

EXAMPLE A:

Tablets

A mixture of 1 kg of 3-(4-phenyl-1,2,3,6-tetrahydro-1=pyridylmethyl)-1,2,3,4-tetrahydrocarbazole, 4 kg of lactose, 1.2 kg of potato starch, 0.2 kg of talc and 0.1 kg of magnesium stearate is compressed to form tablets in a customary manner so that each tablet contains 10 mg of active compound.

EXAMPLE B

Coated tablets

Tablets are formed by compression in analogy to Example A and these are then coated in a customary manner with a coating of sucrose, potato starch, talc, tragacanth and colorant.

EXAMPLE C

Capsules 2 kg of 3-(4-phenyl-1,2,3,6-tetrahydro-1-pyridylmethyl)-6-hydroxy-1,2,3,4-tetrahydrocarbazole are filled into hard gelatine capsules in a customary manner so that each capsule contains 20 mg of the active compound.

EXAMPLE D

Ampoules

A solution of 1 kg of 3-(4-phenyl-1,2,3,6-tetrahydro-1-pyridylmethyl)-7-hydroxy-1,2,3,4-tetrahydrocarbazole hydrochloride in 30 liters of double distilled water is sterilized by filtration, filled into ampoules, freeze-dried under sterile conditions and sealed sterile. Each ampoule contains 10 mg of active compound.

In analogy, tablets, coated tablets, capsules and ampoules can be obtained which contain one or more of the other active compounds of the formula I and/or their physiologically acceptable acid addition salts.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A tetrahydrocarbazole derivative of the formula

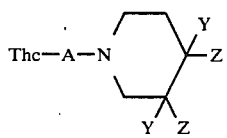

wherein,

Thc is 1,2,3,4-tetrahydro-3-carbazolyl, 1,2,3,4-tetrahydro-3-carbazolyl substituted once or twice by alkyl, O-alkyl, S-alkyl, SO-alkyl, SO$_2$-alkyl, OH, F, Cl, Br, CF$_3$ or CN or by a methylenedioxy group;

the two radicals Y together form a C-C bond;

one radical Z is Ar and the other radical Z is H;

A is —CH$_2$— or —CH$_2$CH$_2$—; and

Ar is phenyl, phenyl substituted once or twice by alkyl, O-alkyl, S-alkyl, SO-alkyl, SO$_2$-alkyl, OH, F, Cl, Br, CF$_3$ or CN or by a methylenedioxy group, or is 2- or 3-thienyl;

all alkyl groups each have 1-4 C atoms;

or a physiologically acceptable acid addition salt thereof.

2. (a) 3-(4-Phenyl-1,2,3,6-tetrahydro-1-pyridylmethyl)-1,2,3,4-tetrahydrocarbazole;

(b) 3-(4-Phenyl-1,2,3,6-tetrahydro-1-pyridylmethyl)-6-hydroxy-1,2,3,4-tetrahydrocarbazole;

(c) 3-(4-Phenyl-1,2,3,6-tetrahydro-1-pyridylmethyl)-7-hydroxy-1,2,3,4-tetrahydrocarbazole;

each a compound of claim 1.

3. A compound of claim 1, wherein each alkyl is methyl.

4. A compound of claim 1, wherein Thc is unsubstituted.

5. A compound of claim 1, wherein Thc is substituted once, in the 6- or 7-position by —CH$_3$, —C$_2$H$_5$, —OCH$_3$, —OC$_2$H$_5$, —SCH$_3$, —SC$_2$H$_5$, OH, F, Cl, Br, —CF$_3$ or —CN.

6. A compound of claim 1, wherein A is —CH$_2$—.

7. A compound of claim 1, wherein Ar is phenyl.

8. A compound of claim 1, wherein Ar is monosubstituted by —CH$_3$, F, Cl, Br or —CF$_3$.

9. A compound of claim 1, wherein Thc is 1,2,3,4-tetrahydro-3-carbazoyl, methyl-1,2,3,4-tetrahydro-3-carbazolyl, methoxy-1,2,3,4-tetrahydro-3-carbazolyl, dimethoxy-1,2,3,4-tetrahydro-3-carbazolyl, hydroxy-1,2,3,4-tetrahydro-3-carbazolyl, dihydroxy-1,2,3,4-tetrahydro-3-carbazolyl, fluoro-1,2,3,4-tetrahydro-3-carbazolyl, chloro-1,2,3,4-tetrahydro-3-carbazolyl, dichloro-1,2,3,4-tetrahydro-3-carbazolyl, bromo-1,2,3,4-tetrahydro-3-carbazolyl, cyano-1,2,3,4-tetrahydro-3-carbazolyl or methylenedioxy-1,2,3,4-tetrahydro-3-carbazolyl, and the substituents are in the 6- or 7-position.

10. A compound of claim 1, wherein Thc is 1,2,3,4-tetrahydro-3-carbazolyl, 6- or 7- methyl-1,2,3,4-tetrahydro-3-carbazolyl, 6,7-dimethyl-1,2,3,4-tetrahydro-3-carbazolyl, 6- or 7-methoxy-1,2,3,4-tetrahydro-3-carbazolyl, 6,7-dimethoxy-1,2,3,4-tetrahydro-3-carbazolyl, 6- or 7-chloro-1,2,3,4-tetrahydro-3-carbazolyl, 6- or 7-hydroxy-1,2,3,4-tetrahydro-3-carbazolyl, 6,7-dihydroxy-1,2,3,4-tetrahydro-3-carbazolyl or 6,7-methylenedioxy-1,2,3,4-tetrahydro-3-carbazolyl.

11. A compound of claim 1, wherein Ar is phenyl, tolyl, methoxyphenyl, fluorophenyl, chlorophenyl, trifluoromethylphenyl or chlorotrifluoromethylphenyl.

12. A compound of claim 1, wherein Thc is 1,2,3,4-tetrahydro-3-carbazolyl, 6- or 7-methoxy-1,2,3,4-tetrahydro-3-carbazolyl, 6- or 7-hydroxy-1,2,3,4-tetrahydro-3-carbazolyl, 6,7-dimethoxy-1,2,3,4-tetrahydro-3carbazolyl, 6- or 7-chloro-1,2,3,4-tetrahydro-3-carbazolyl or 6,7-dihydroxy-1,2,3,4-tetrahydro-3-carbazolyl.

13. A compound of claim 1, wherein Thc is 1,2,3,4-tetrahydro-3-carbazolyl, or 6- or 7-hydroxy-1,2,3,4-tetrahydro-3-carbazolyl.

14. A composition comprising a compound of claim 1, and a pharmacologically acceptable carrier.

15. A composition comprising 0.2–500 mg of a compound of claim 1 and a pharmacologically acceptable carrier.

* * * * *